(12) United States Patent
Kusumoto

(10) Patent No.: US 10,973,436 B2
(45) Date of Patent: Apr. 13, 2021

(54) PERICARDIOCENTESIS NEEDLE GUIDED BY CARDIAC ELECTROPHYSIOLOGY MAPPING

(71) Applicant: Walter Kusumoto, Chico, CA (US)

(72) Inventor: Walter Kusumoto, Chico, CA (US)

( * ) Notice: Subject to any disclaimer, the term of this patent is extended or adjusted under 35 U.S.C. 154(b) by 461 days.

(21) Appl. No.: 15/713,307

(22) Filed: Sep. 22, 2017

(65) Prior Publication Data

US 2018/0078172 A1 Mar. 22, 2018

Related U.S. Application Data

(60) Provisional application No. 62/398,394, filed on Sep. 22, 2016, provisional application No. 62/516,556, filed on Jun. 7, 2017.

(51) Int. Cl.
| | | |
|---|---|---|
| *A61B 5/06* | (2006.01) | |
| *A61B 34/20* | (2016.01) | |
| *A61B 5/287* | (2021.01) | |
| *A61B 5/00* | (2006.01) | |
| *A61B 5/055* | (2006.01) | |

(52) U.S. Cl.
CPC .............. *A61B 5/065* (2013.01); *A61B 5/062* (2013.01); *A61B 5/287* (2021.01); *A61B 5/6848* (2013.01); *A61B 5/6869* (2013.01); *A61B 5/7445* (2013.01); *A61B 34/20* (2016.02); *A61B 5/055* (2013.01); *A61B 5/063* (2013.01); *A61B 5/743* (2013.01); *A61B 5/7425* (2013.01); *A61B 2034/2053* (2016.02)

(58) Field of Classification Search
CPC ....... A61B 5/065; A61B 34/20; A61B 5/0422; A61B 5/062; A61B 5/6848; A61B 5/6869; A61B 5/7445; A61B 2034/2053; A61B 5/055; A61B 5/063; A61B 5/7425; A61B 5/743
USPC ........................................................ 600/508
See application file for complete search history.

(56) References Cited

U.S. PATENT DOCUMENTS

| | | |
|---|---|---|
| 5,405,376 A | 4/1995 | Mulier |
| 6,026,316 A * | 2/2000 | Kucharczyk ........ A61M 31/005 324/309 |
| 6,165,164 A | 12/2000 | Hill |
| 6,171,303 B1 | 1/2001 | Ben-Haim |
| 6,206,874 B1 | 3/2001 | Ubby |
| 6,318,375 B1 | 11/2001 | Plicchi |
| 6,496,712 B1 | 12/2002 | Dahl |

(Continued)

*Primary Examiner* — Aaron F Roane
(74) *Attorney, Agent, or Firm* — Heisler & Associates

(57) ABSTRACT

The pericardiocentesis needle is fitted with sensors, such as at least one electrode or at least one magnetic field sensor, and preferably both a proximal and a distal electrodes or multiple magnetic field sensors. These electrodes or other sensors are coupled to an electrophysiology mapping system configured to display cardiac structures on a display. The electrodes or other sensors on the needle cause a position, and preferably also orientation, of the needle, and especially the tip of the needle, to be visualized on a display of the electrophysiology mapping system, in accurate position relative to adjacent cardiac structures. In other embodiments other transcutaneous devices such as dilators and sheaths can be similarly fitted with electrodes or other sensors for visualization of such other devices within a display of an EP mapping system.

18 Claims, 5 Drawing Sheets

(56) References Cited

U.S. PATENT DOCUMENTS

| | | | |
|---|---|---|---|
| 6,892,091 B1 * | 5/2005 | Ben-Haim | A61B 5/0422 600/509 |
| 7,815,577 B2 | 10/2010 | Krishnan | |
| 7,917,216 B1 | 3/2011 | Ryu | |
| 8,010,186 B1 | 8/2011 | Ryu | |
| 8,050,739 B2 | 11/2011 | Eck | |
| 8,172,757 B2 | 5/2012 | Jaffe | |
| 8,285,364 B2 | 10/2012 | Barbagli | |
| 8,287,531 B2 | 10/2012 | Mest | |
| 8,326,419 B2 | 12/2012 | Rosenberg | |
| 8,388,549 B2 | 3/2013 | Paul | |
| 8,403,925 B2 | 3/2013 | Miller | |
| 8,406,866 B2 | 3/2013 | Deno | |
| 8,755,864 B2 | 6/2014 | Hauck | |
| 8,825,144 B2 | 9/2014 | Starks | |
| 2003/0083560 A1 * | 5/2003 | Osypka | A61N 1/056 600/374 |
| 2006/0253032 A1 | 11/2006 | Altmann | |
| 2007/0021648 A1 | 1/2007 | Lenker | |
| 2007/0106208 A1 * | 5/2007 | Uber, III | A61J 1/1443 604/65 |
| 2008/0177138 A1 | 7/2008 | Courtney | |
| 2008/0183072 A1 | 7/2008 | Robertson | |
| 2009/0171196 A1 | 7/2009 | Olson | |
| 2011/0087105 A1 | 4/2011 | Ridley | |
| 2011/0087175 A1 | 4/2011 | Krishnan | |
| 2011/0098564 A1 | 4/2011 | Larson | |
| 2012/0143045 A1 * | 6/2012 | Klingenbeck | A61B 6/12 600/424 |
| 2012/0172717 A1 * | 7/2012 | Gonda | A61B 5/042 600/424 |
| 2013/0241929 A1 | 9/2013 | Massarwa | |
| 2014/0148688 A1 | 5/2014 | Ludwin et al. | |
| 2014/0257102 A1 | 9/2014 | Hossack | |
| 2015/0289781 A1 | 10/2015 | Grunwald | |
| 2017/0172457 A1 * | 6/2017 | Govari | A61M 25/0127 |

* cited by examiner

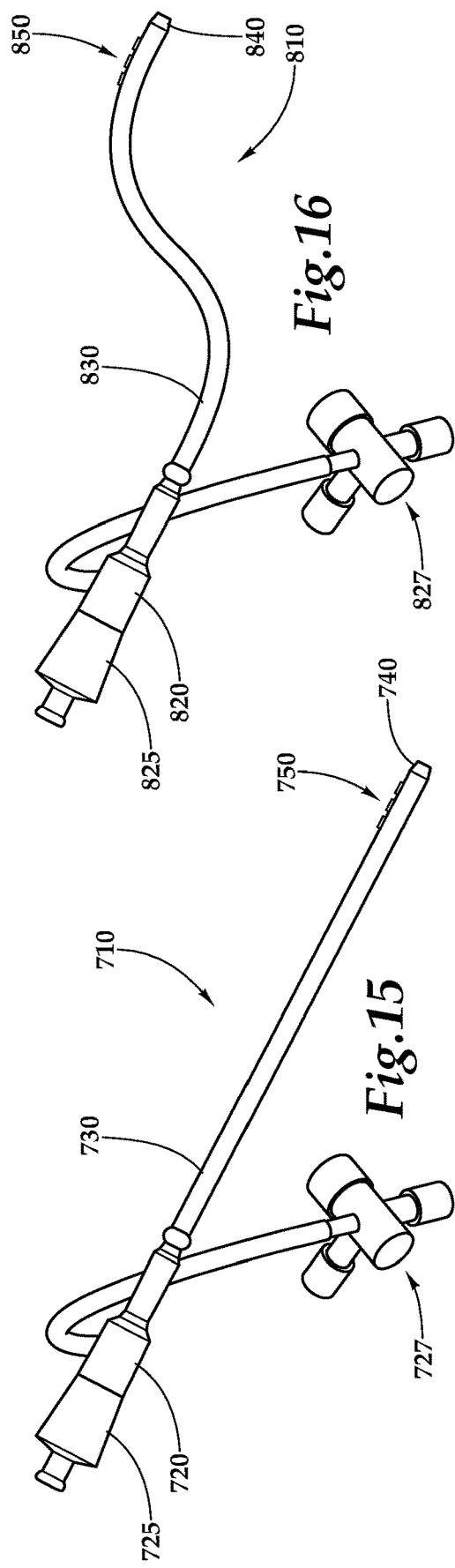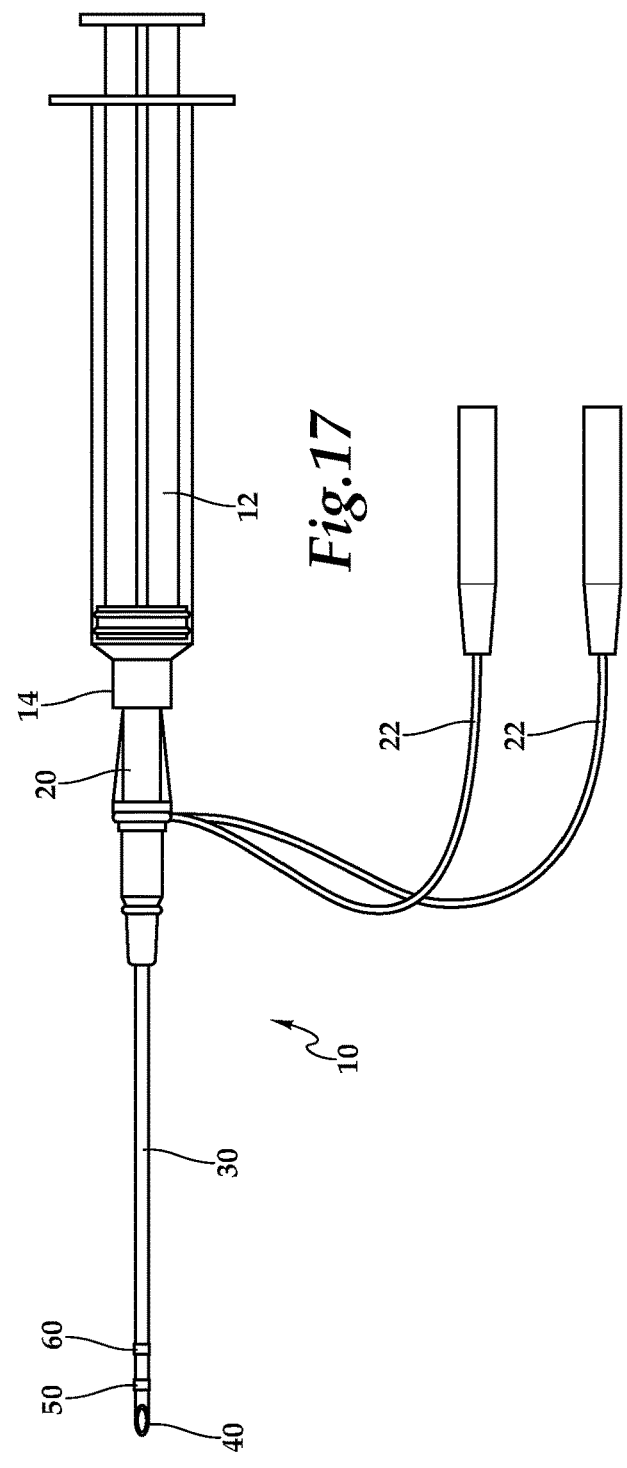

PERICARDIOCENTESIS NEEDLE GUIDED BY CARDIAC ELECTROPHYSIOLOGY MAPPING

CROSS-REFERENCE TO RELATED APPLICATIONS

This application claims benefit under Title 35, United States Code § 119(e) of United States Provisional Application No. 62/398,394 filed on Sep. 22, 2016 and United States Provisional Application No. 62/516,556 filed on Jun. 7, 2017.

FIELD OF THE INVENTION

The following invention relates to pericardiocentesis needles and other interventional devices, including dilators and sheaths, which are modified to include sensors thereon so that the position of the needle or other interventional device can be visualized subcutaneously during a cardiac procedure using cardiac electrophysiology mapping systems. More particularly, this invention relates to needles and similar interventional devices which are fitted with one or more electrodes or one or more magnetic field sensors so that the needles or other interventional devices can be displayed in an accurate position (and preferably also orientation) within an electrophysiology mapping system display.

BACKGROUND OF THE INVENTION

Pericardiocentesis was first introduced in 1840, and has been continually refined to the present. This technique involves placing a needle into the chest and entering the pericardial sac which surrounds the heart. Fluid in this space can give clues on diagnosis of multiple pathologies, and can relieve potentially catastrophic consequences. Pericardiocentesis can be both diagnostic and therapeutic especially for pericardial tamponade which is a life threatening condition that can occur spontaneously during electrophysiology study and ablation. Serious complications of pericardiocentesis are not uncommon, including injury to the liver, myocardium, coronary arteries and lungs. Echo guidance for pericardiocentesis has become a standard, however there are difficulties in performing transthoracic echo or intravascular echo while simultaneously directing a pericardiocentesis needle. Fluoroscopy is sometimes utilized, but exposes both patient and operator to radiation. CT and MRI guidance have been reported, however would require access to CT/MRI which may not be readily available in the cardiac catheterization lab.

The advent of epicardial mapping and ablation, and percutaneous epicardial left atrial appendage closure requires entering the pericardial space without significant pericardial fluid. Without significant pericardial fluid, the pericardiocentesis needle can enter the myocardium or coronary artery without having a buffer of collected pericardial fluid. This situation is a more difficult technique for the operator, and possibly has increased risk of catastrophic complications.

Various commercially available cardiac electrophysiology mapping systems use different modalities to identify locality of catheters within the body. The St. Jude ENSITE system, a trademark of St. Jude Medical, Atrial Fibrillation Division, Inc. of St. Paul, Minn., uses impedance to localize various catheters relative to a stable catheter located within the heart. There is a background circuit utilizing a high frequency transthoracic electric field between the catheters and body surface electrodes, which detect impedance changes relative to a stable cardiac catheter (usually located within the coronary sinus) to derive location information within the heart. Consequently, this existing cardiac electrophysiology mapping system can utilize bipolar/unipolar electrode impedance and/or electrical current to determine the location of these electrodes in a three-dimensional space relative to a set of reference electrodes.

Another mapping system produced by Biosense Webster utilizes a magnetic field and a magnetic sensor to localize catheter location. A magnetic field is created around the thorax, and a magnetic sensor equipped catheter within this three-dimensional field is localized to a precision within 1 mm. These mapping systems can combine anatomical information from computer tomographic imaging, fluoroscopy and intravascular echo into the electrical mapping system. These include endocardial, epicardial and importantly pericardial structures, without the need of active fluoroscopy.

SUMMARY OF THE INVENTION

With this invention, a needle or dilator or other interventional device is fitted with at least one, and preferably with a pair electrodes utilizing impedance and/or electrical current data or a magnetic sensor within a magnetic field to localize the needle tip during pericardiocentesis or related procedures. This magnetic sensor or electrode in conjunction with existing cardiac electrophysiology mapping systems allows for direct/real time visualization of the entrance of the needle tip and dilator tip into the pericardial space. In addition, the cardiac electrophysiology mapping system can combine fluoroscopy, computer tomographic imaging and/or intravascular echo to further delineate epicardial/pericardial space and extracardiac structures during pericardiocentesis.

Electrophysiology mapping (hereafter EP mapping) systems are provided from multiple sources, and generally allow for an intra-vascular/intra-cardio catheter and/or electrode to have its location visualized within the heart. With this invention, a pericardiocentesis needle is outfitted in one of a variety of different manners, at least some of which are similar to the outfitting of catheters and/or electrodes within an EP mapping system which are placed intra-vascularly into or proximate to the interior of the heart. The pericardiocentesis needle is thus modified from prior pericardiocentesis needles to include at least one electrode thereon or some other sensor, such as a magnetic field sensor. This sensor, such as an electrode, is routed into the EP mapping system, such as in the same way that other electrodes or other sensors within an EP mapping system are integrated into the EP mapping system, such as the way that catheters and intra-venus electrodes of EP mapping systems are connected into such EP mapping systems for visualization thereof on a display of the the EP mapping system. One such EP mapping system is disclosed in U.S. Pat. No. 8,825,144, incorporated herein by reference in its entirety.

The methodology implemented by this mapping system is based on the principle that when electrical current is applied across two surface electrodes, a voltage gradient is created along the axis between the electrodes. Although any suitable number of electrodes may be utilized, typically six surface electrodes are placed on the body of the patient and in three pairs: anterior to posterior, left to right lateral, and superior (neck) to inferior (left leg). The three electrode pairs form three orthogonal axes (X-Y-Z), with the patient's heart being at least generally at the center.

These six surface electrodes are connected to the EP mapping system. In embodiments, such as those working with the St. Jude ENSITE EP mapping system, the various electrodes alternately send an electrical signal through each pair of surface electrodes to create a voltage gradient along each of the three axes, forming a transthoracic electrical field. Conventional electrophysiology catheters may be connected to the system and advanced to the patient's heart. As a catheter enters the transthoracic field, each catheter electrode senses voltage, timed to the creation of the gradient along each axis. Using the sensed voltages compared to the voltage gradient on all three axes, the three-dimensional position of each catheter electrode is calculated. The calculated position for the various electrodes can occur simultaneously and be repeated many times per second.

The EP mapping system can display the located electrodes as catheter bodies with real-time navigation. By tracking the position of the various catheters, the system provides non-fluoroscopic navigation, mapping, and creation of chamber models that are highly detailed and that have very accurate geometries. In the latter regard, the physician sweeps an appropriate catheter electrode across the heart chamber to outline the structures by relaying the signals to the computer system that then generates the 3-D model. This 3-D model may be utilized for any appropriate purpose, for instance to help the physician guide an ablation catheter to a heart location where treatment is desired.

In order to generate an accurate and highly detailed map of a patient's heart, a large amount of data is required. Accordingly, an electrode catheter may be swept across various surfaces of the heart while obtaining data as described above. In order to accelerate this mapping data acquisition and/or increase the volume of data available for mapping, a number of high-density electrode catheters have been developed or proposed. Generally, these include a number of electrodes in an array in relation to a catheter body so as to substantially simultaneously obtain many mapping data points for a corresponding surface of cardiac tissue proximate to the catheter body. For example, these electrodes may be deployed along the length of a section of the catheter body that has a coil or other three-dimensional configuration so as to provide the desired spatial distribution of the electrodes. Alternatively, the electrodes may be disposed on a number of structural elements extending from a catheter body, e.g., in the form of a basket or a number of fingers.

Once the mapping data has been acquired, software may be implemented to generate multiple surface images, which when combined, comprise a three-dimensional image of the patient's heart. This image can be displayed on a suitable output device in real-time so that the physician can "see" the patient's heart and the catheter for properly positioning the catheter at a work site within the patient's heart for a medical procedure (e.g., an ablation procedure).

The electrode or other sensor on the needle causes the location of the electrode relative to adjacent cardiac structures to be visualized on the display of the EP mapping system. By placing the electrode on the needle a known distance from a tip of the needle, and by knowing the orientation of the needle, the precise location of the tip of the needle can be known and visualized on the EP mapping system display. Knowing orientation of the needle can occur by having multiple electrodes on the needle, one distal and one proximal, so that the orientation of the needle is merely a line segment between the position of the two electrodes, or can be ascertained in some other fashion, such as by having a needle orientation sensor placed on the needle itself or other sensor physically attached to the needle. In one embodiment one of the electrodes can be the tip of the needle itself. By visualizing on the display the location of the tip of the pericardiocentesis needle in real time, a surgeon or other medical professional can precisely place the tip of the pericardiocentesis needle where desired relative to adjacent cardiac structures.

In certain environments, other imaging systems can be incorporated along with the EP mapping system, such as CT scans, MRI scans, ultrasound, fluoroscopy, etc. While the invention is described above in particular with regard to pericardiocentesis needles, other interventional devices have a transcutaneous nature can similarly be outfitted with electrodes or other sensors and integrated into the EP mapping system for visualization of location (and preferably also orientation) of such other devices. Such other devices include dilators, sheaths, catheters, stylets associated with needles and dilators, and other transcutaneous interventional devices. When EP mapping systems are referenced, these can be electric field based or magnetic field based, as described above (or some combination thereof).

OBJECTS OF THE INVENTION

Accordingly, a primary object of the present invention is to provide a pericardiocentesis needle or other transcutaneous interventional device which is fitted with electrodes are other sensors so that it can be visualized through an EP mapping system display for most accurate, reliable and safe placement of the tip of the needle or other device.

Another object of the present invention is to provide a pericardiocentesis needle with at least one electrode thereon coupled to an EP mapping system with location of the needle presented within a display of the system.

Another object of the present invention is to provide a method for more effectively performing pericardiocentesis procedures, especially after pericardial fluid has been reduced.

Another object of the present invention is to provide a needle equipped with bipolar/unipolar electrodes which can monitor impedance and/or electrical current for positioning the needle in an EP mapping system display.

Another object of the present invention is to provide a system where the impedance and/or electrical current data from sensors on the needle or other device can be utilized by existing cardiac electrophysiology mapping technologies to visualize the needle tip entry into the pericardial space.

Another object of the present invention is to provide a needle equipped with at least one magnetic sensor to convey locational information in a magnetic field.

Another object of the present invention is to provide magnetic data that can be utilized by existing cardiac electrophysiology mapping technologies to visualize the needle tip entry into the pericardial space.

Another object of the present invention is to provide a dilator equipped with bipolar/unipolar electrode pair or other sensors which can monitor impedance and/or electrical current for positioning the dilator in an EP mapping system display.

Another object of the present invention is to provide impedance and/or electrical current data that can be utilized by existing cardiac electrophysiology technologies to visualize the dilation of the pericardial sac and confirm entry of a J wire into the pericardial space.

Another object of the present invention is to provide a dilator equipped with at least one magnetic sensor to convey locational information in a magnetic field.

Another object of the present invention is to provide magnetic data that can be utilized by existing cardiac EP mapping technologies to visualize dilator entry into the pericardial space.

Another object of the present invention is to provide a sheath equipped with at least one magnetic sensor to convey locational information in a magnetic field.

Another object of the present invention is to provide magnetic data that can be utilized by existing cardiac EP mapping technologies to visualize sheath entry into the pericardial space.

Other further objects of the present invention will become apparent from a careful reading of the included drawing figures, the claims and detailed description of the invention.

BRIEF DESCRIPTION OF THE DRAWINGS

FIG. 15 is a perspective view of a sheath assembly with magnetic field sensors shown thereon as one form of sensors for visualizing a location of a tip of the sheath assembly according to one embodiment of this invention.

FIG. 16 is a perspective view of that which is shown in FIG. 15, but for a sheath having a curving contour.

FIG. 17 is a front elevation view of a variation of the needle of FIG. 3 with a syringe attached to a hub of the needle and with leads extending from the hub for interfacing into an EP mapping system.

DESCRIPTION OF THE PREFERRED EMBODIMENT

Figure 1:
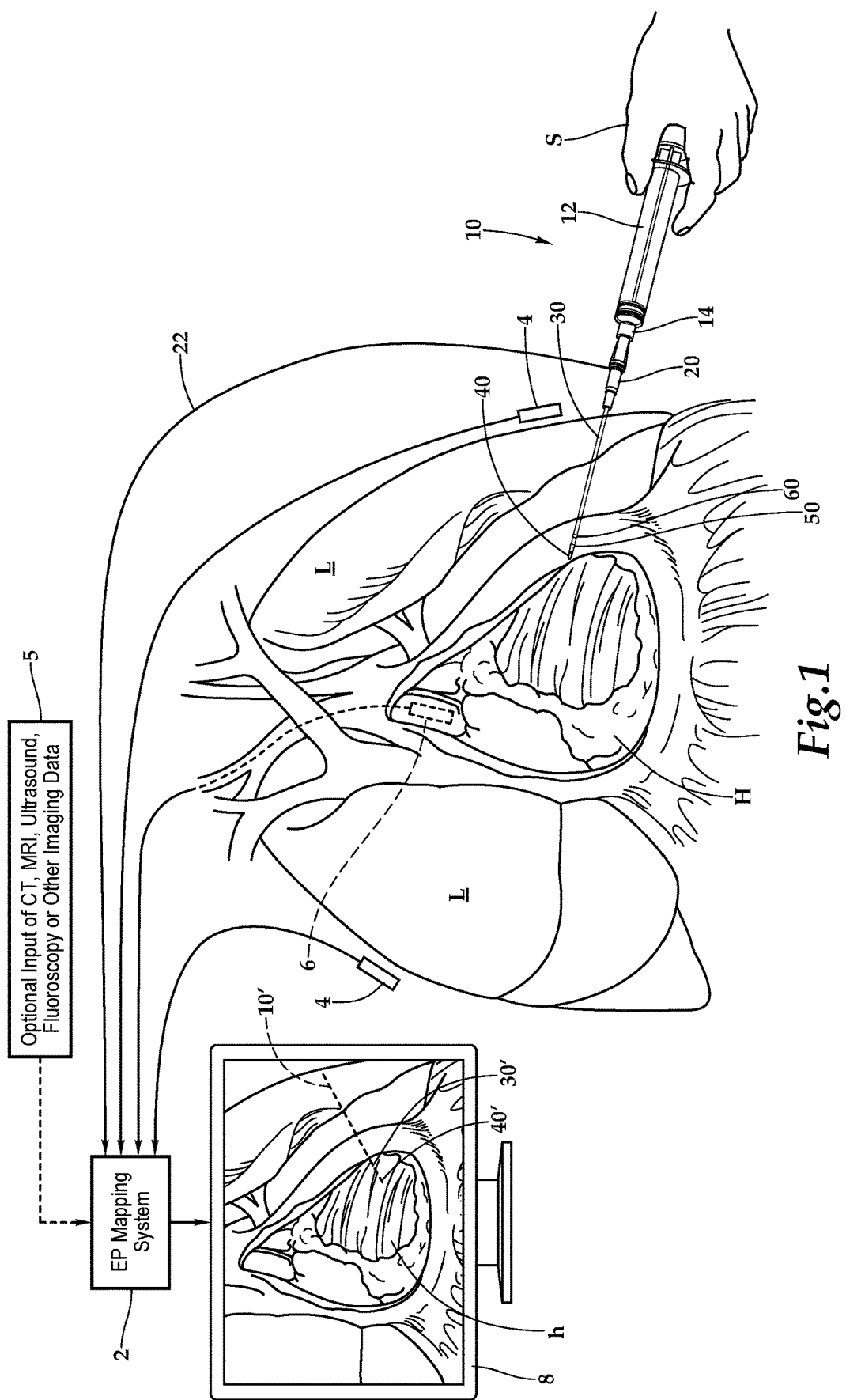
FIG. 1 is a schematic depiction of the system of this invention including a portion of a torso of a patient with a pericardiocentesis needle fitted with sensors in the form of electrodes shown engaging bodily structures proximate to the heart of a patient, and while the needle is visualized on a display of an EP mapping system, the EP mapping system relying primarily upon electrodes for generating the image displayed on the EP mapping system display.

Referring to the drawings, wherein like reference numerals represent like parts throughout the various drawing figures, reference numeral 10 is directed to a pericardiocentesis needle (FIGS. 1-6 and 17) which provides one form of a transcutaneous medical device with sensors, such as electrodes 50, 60, on the needle 10 to cause the needle 10 to be visualizable on a display 8 of an electrophysiology (EP) mapping system 2. The needle 10 or other medical device can thus be accurately placed into spaces such as the pericardium while a tip 40 of the needle 10 can be visualized on the display 8, to assist in navigation of the needle 10 to a desired position, especially for the tip 40.

In essence, and with particular reference to FIG. 1, basic details of the needle 10 and associated EP mapping system 2 as modified by one embodiment of this invention, is described. The EP mapping system 2 includes multiple surface electrodes 4, as well as intra-cardiac electrodes 6 (and optionally also auxiliary input 5 of imaging data) to gather data for presentation on a display 8. The needle 10 is modified according to this invention so that it can be visualized on the display 8 of the EP mapping system 2. The needle 10 includes a hub 20 with a shaft 30 extending from the hub 20 to a tip 40. In this embodiment, at least one electrode, and preferably both a distal electrode 50 and proximal electrode 60, are placed along the shaft 30. These two electrodes 50, 60 measure electric field intensity (or current or other electrical properties) and supply this information to the EP mapping system 2 so that a position, and also preferably orientation, of the needle 10 can be determined and be displayed on the display 8, and especially a location of the tip 40 of the needle 10 relative to other cardiac structures included on the display 8.

Figure 2:
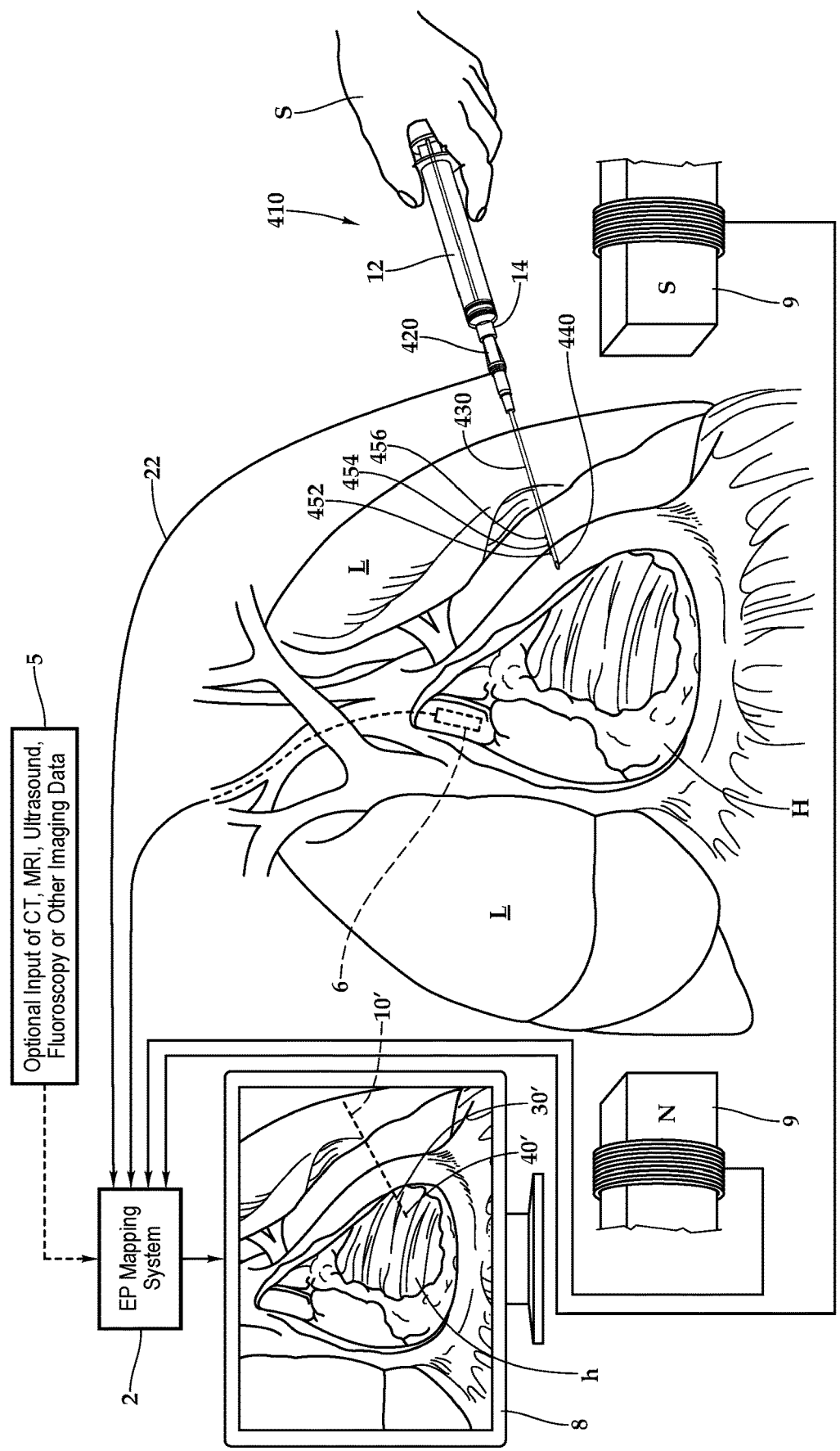
FIG. 2 is a schematic similar to that depicted in FIG. 1, but for an EP mapping system which primarily generates an image of cardiac structures based on placement of a magnetic field proximate to the patient and utilizing magnetic field sensors to localize the pericardiocentesis needle within the image displayed by the EP mapping system.

More specifically, and with particular reference to FIGS. 1 and 2, basic details of various EP mapping systems 2 are described, with which the needle 10 or other medical device of this invention is configured to interoperably perform. The EP mapping system 2 can be any of a variety of different medical visualization systems, but most preferably those which utilize electric and or magnetic fields to determine the location of bodily structures, and in this case, particularly cardiac structures of a patient.

As a general outline, the EP mapping system 2 can include a plurality of electrodes 4 in the form of surface electrodes on a surface of the patient. FIG. 1 depicts two such surface electrodes 4, but typically more than two such surface electrodes 4 would be utilized. Also, an intracardiac electrode 6 is typically also passed intravenously to a position within or adjacent to the heart H of the patient.

As explained in detail hereinabove, in one embodiment certain pairs of electrodes, such as the surface electrodes 4, switch between providing an excitation voltage resulting in the production of an electric field, and operating in a sensing mode wherever the electrodes sense voltage and/or current or other electrical properties at the locations of various electrodes. Together these electrodes, when switching between an excitation function and a sensing function, gather data about cardiac structures and other subcutaneous structures having different electrical properties, which data is converted into imagery suitable for presentation on the display 8 of the EP mapping system 2.

In one embodiment depicted in FIG. 2, the EP mapping system 2 either replaces the electrodes 4, 6 with magnetic field inducing elements such as magnets 9, or such magnetic field sources 9 augment an EP mapping system 2 which also includes electrodes 4, 6. Furthermore, cardiac structural data can be augmented with information from an auxiliary imaging source 5 and put into the EP mapping system 2. Such auxiliary input 5 can be provided from imaging devices such as computer tomography (CT), magnetic resonance imaging (MRI), ultrasound, fluoroscopy, or other imaging data.

Importantly with this invention, and as described below, the needle 10 or other transcutaneous medical device is fitted with electrodes 50, 60 or other sensors so that a position (and also preferably orientation) of the needle 10, and especially a tip 40 of the needle 10 can be visualized on the display 8 at an accurate position adjacent to heart H structures so that a position (and also preferably orientation) of the needle 10, and especially a tip 40 of the needle 10 can be visualized on the display 8 at an accurate position adjacent to the heart H and other bodily structures. On the display 8, the needle 10 appears as the needle 10' with the tip 40 appearing as a tip 40' and the shaft 30 of the needle 10 appearing as shaft 30'. A user, such as a surgeon S, can thus accurately position the needle 10 by viewing the display 8 of the EP mapping system 2 and moving the needle 10 to cause the tip 40 to be positioned where desired, while watching the display 8.

With continuing reference to FIG. 1, as well as FIG. 17, the needle 10 is described according to an initial exemplary embodiment. The needle 10 includes the hub 20 which supports the shaft 30 extending from the hub 20 to a tip 40. The hub 20 is configured to attach to other fluid handling structures, such as a syringe 12, such as through a luer fitting 14. The hub 20 also preferably has leads 22 which can extend to the EP mapping system 2, and which also connect to electrodes (or other sensors) on the needle 10. In this initial exemplary embodiment, the electrodes include a distal electrode 50 and a proximal electrode 60. By providing two electrodes 50, 60, when their position is determined a line segment between these two electrodes 50, 60 defines a central axis of the shaft 30 of the needle 10. Also, by knowing a distance that the tip 40 is spaced away from the distal electrode 50 (or other reference point), a position of the tip 40 can be precisely determined. This information can be superimposed into the imaging data set which is displayed in the display 8 of the EP mapping system 2, so that a needle 10', as well as a tip 40' of the shaft 30' can all be visualized (FIG. 1), even though no electrode is at the tip 40 of the needle 10.

While it is conceivable that the electrodes 50, 60 could have their own power supply and transmit signals associated therewith wirelessly to the EP mapping system 2, typically the electrodes 50, 60 are connected by a conducting wire 52, 62 from the electrodes 50, 60 through the leads 22 to the EP mapping system 2. FIG. 17 shows two such leads 22 which couple to the wires 52, 62 (FIG. 3) and which lead to the EP mapping system 2, such as along lead 22 (shown as a single line for convenience).

Figure 3:
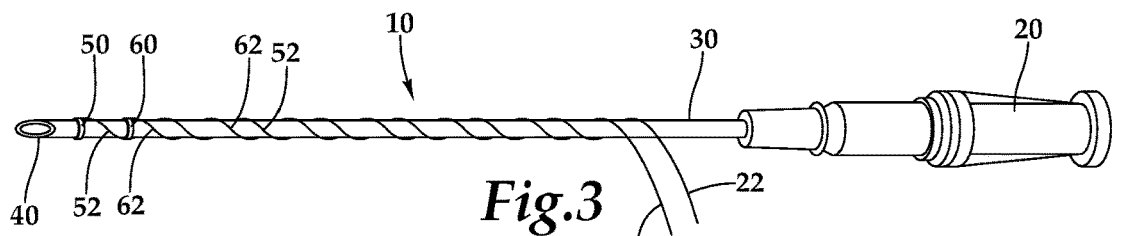
FIG. 3 is a perspective view of a pericardiocentesis needle according to a first embodiment of this invention.
Figure 5:
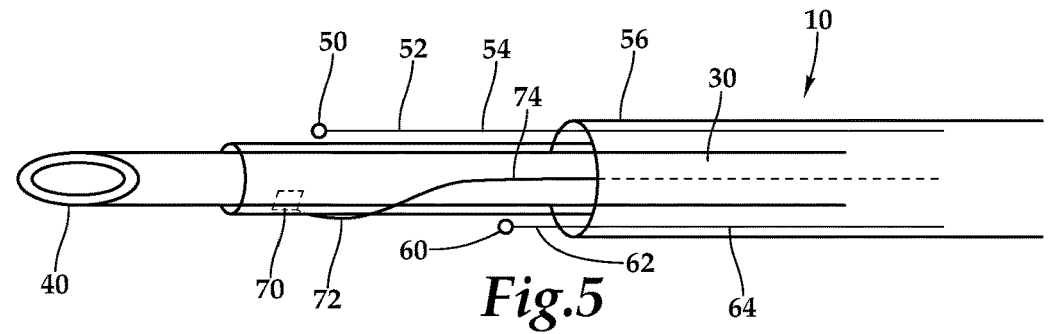
FIG. 5 is a detail of a portion of that which is shown in FIG. 3, and with electrodes shown schematically.

With particular reference to FIG. 3, a simplest form of the needle 10 with two electrodes 50, 60 coupleable to the EP mapping system 2 through external wires 52, 62 is disclosed. These wires 52, 62 are just left external to the shaft 30 of the needle 10 in this embodiment. Such an embodiment would typically perhaps only be used for testing, but could conceivably be utilized for therapeutic purposes. The wires 52, 62 might conceivably be left without any insulation jacket 54, 64 around the wires 52, 62, especially if the shaft 30 of the needle 10 is formed of a non-conducting material. However, typically these wires 52, 62 are encased within their own insulation jackets 54, 64 (FIG. 5). Also, these wires 52, 62 are preferably contained within an outer insulation 56 lining which holds the wires 52, 62 directly adjacent to the shaft 30.

Electrodes 50, 60 themselves could have any of a variety of different configurations, including configurations where they are flush with a surface of the shaft 30 of the needle 10, and embodiments where these electrodes 50, 60 extend outwardly, at least somewhat. In FIGS. 1-4, these electrodes 50, 60 are depicted as having a torroidal form and extending only very slightly away from the surface of the shaft 30. Most preferably, these electrodes 50, 60 are isolated from the shaft 30 of the needle 10 itself. For instance, and as depicted in FIG. 5, an inner lining of insulation can be provided directly adjacent to the shaft 30 of the needle 10. The electrodes 50, 60 are outboard of this innermost insulation lining. The wires 52, 62 are preferably provided with insulation jackets 54, 64 so that if these wires 52, 62 come into contact with each other, electric current is prevented from flowing therebetween. Finally, the outer insulation 56 is preferably provided to encase the wires 52, 62 and their associated insulation jackets 54, 64 are isolated from surrounding structures that the needle 10 might come in contact with. If the shaft 30 of the needle 10 is formed of non-conductive material, the innermost layer of insulation (FIG. 5) can be dispensed with.

The two electrodes 50, 60 are preferably provided a known distance apart from each other and with the distal electrode 50 a known distance away from the tip 40. For instance, the distal electrode 50 can be one inch away from the tip 40 and the proximal electrode 60 can be placed one inch away from the distal electrode 50. Such known distances between the electrodes 50, 60 and away from the tip 40 allow for accurate visualization of location and orientation of the tip 40 of the needle 10 on the display 8. As an example, if the shaft 30 of a needle 10 is extending along a central axis, with a proximal electrode 60 at an origin on the central axis, and the distal electrode 50 is at a one inch mark on this axis, it is known that the tip 40 will be at the two inch mark on this central axis. The coordinates of this central axis can be associated with what is fed to the display 8, and not only the positions of the electrodes 50, 60 can be provided, but also a virtual needle 10' can be animated and presented on the display 8, with the needle 10' extending right up to the tip 40'.

Bodily structures on the display 8 might hide the needle 10' at least somewhat. Known techniques with EP mapping systems 2 can be utilized to make sure that important structures can still be visualized. As one option, body structures "in front of" the portions of the needle 10' adjacent to the tip 40' can be cut away so that the tip 40' of the needle 10' can be seen. As another alternative, at least portions of the needle 10' can be shown in a phantom or broken line manner which perhaps becomes more pronounced or less pronounced based on a depth of the needle away from a view and perspective point, to represent depth. As another option, video editing tools can be utilized by a user to selectively remove bodily structures presented on the display 8 in a customizable fashion to display what the surgeon S or other medical practitioner wants to see, but remove enough detail so that important portions of the needle 10' can be clearly seen.

Figure 4:
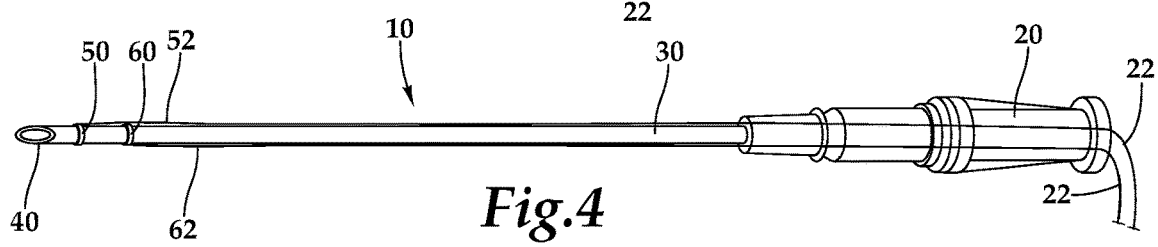
FIG. 4 is a perspective view of a modified version of that which is shown in FIG. 3.
Figure 6:
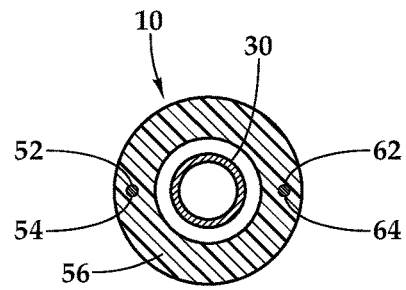
FIG. 6 is an end full sectional view of an embodiment of that which is shown in FIG. 3, which has both a proximal electrode and a distal electrode.

In FIG. 4 a variation of the needle 10 is displayed where the wires 52, 62 are held adjacent to the shaft 30, such as by placement inboard of outer insulation 56 (FIG. 5). The wires 52, 62 coupled to the electrodes 50, 60 are routed through the hub 20 in this embodiment, where they transition into the leads 22 extending to the EP mapping system. FIG. 5 further depicts, somewhat schematically, how different layers of insulation including innermost insulation and outer insulation 56 are located inboard and outboard of the electrodes 50, 60 and with the outer insulation 56 stopping short of positions for the electrodes 50, 60 so that the electrodes 50, 60 are not blocked from sensing electrical characteristics of bodily structures adjacent to the needle 10 and sensing the electric field sufficiently precisely to allow the electrodes 50, 60 to be located within a three-dimensional space adjacent to the heart H of a patient, without disruption by the electrically insulative character of the other insulation 56. Electrodes in FIG. 5 are seen schematically, rather than with any particular geometric configuration. FIG. 6 depicts how the wires 52, 62 and associated insulation jackets 54, 64 are located outboard of the shaft 30 but inboard of outer insulation 56 which is wrapped around an outer side of the wires 52, 62, or has the wires 52, 62 embedded within the outer insulation 56.

FIG. 5 also shows an optional additional sensor in the form of a force sensor 70. This force sensor 70 can be a strain gauge mounted to the shaft 30 of the needle 10, or some other force sensor 70. The force sensor 70 detects compression forces between the tip 40 and the hub 20. For instance, and especially when the tip 40 is large or less sharp, the tip 40 does not penetrate bodily tissues unless sufficient force is applied. In some instances, it is desirable to penetrate some tissues, but not others. For instance, when performing pericardiocentesis, the skin and surface anatomy, and the pericardium are penetrated, but one does not want to penetrate the myocardium. The force sensor transmits a signal, typically along a wire 72 inside of an insulation jacket 74 to the EP mapping system 2 or to a separate display of needle force. The signal can be calibrated and used to keep the tip 40 of the needle 10 from penetrating structures that require more force than a threshold amount, by having the surgeon S monitor the force sensed by the force sensor 70 and keeping it below the threshold maximum force.

Figure 7:
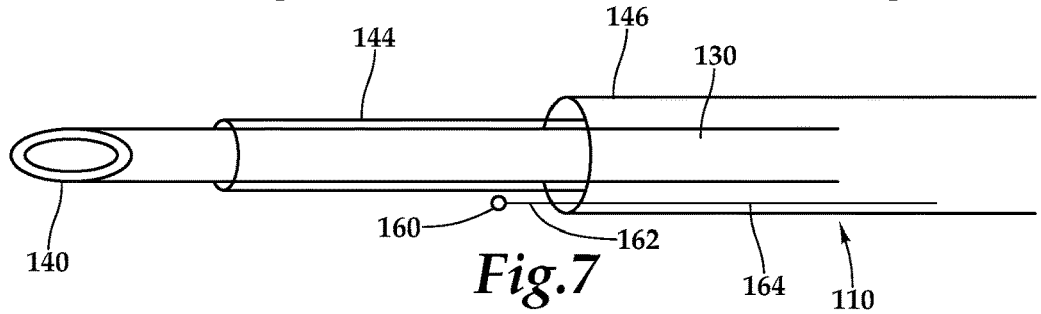
FIG. 7 is a perspective view of an embodiment of that which is shown in FIG. 3 which has a single electrode depicted schematically thereon, and where a tip of the needle can be an electrode.

With particular reference to FIG. 7, details of an alternative embodiment needle 110 are described. This alternative needle 110 is configured so that the tip 140 of the needle 110 can act as a distal electrode. The needle 110 includes a shaft 130 extending to the electrode tip 140. Shaft insulation 144 surrounds the shaft 130. Portions of the shaft 130 extending beyond the shaft insulation 144 generally act as an electrode. Preferably the shaft insulation 144 stops just short of the electrode tip 140, so that an approximation of a singular point can be associated with this electrode tip 140. Preferably in this embodiment, a proximal electrode 160 is also provided which is coupled to a wire 162 which preferably has its own insulation jacket 164. Outer insulation 146 can wrap around the wire 162 to hold the wire 162 adjacent to the shaft 130, but while preventing an electrical connection therebetween. The proximal electrode 160 would preferably be provided at a known distance away from the electric tip 140, so that the needle 110 would generally be effective in a manner similar to other multi-electrode needles such as the needle 10 (FIGS. 1-6).

Figure 9:
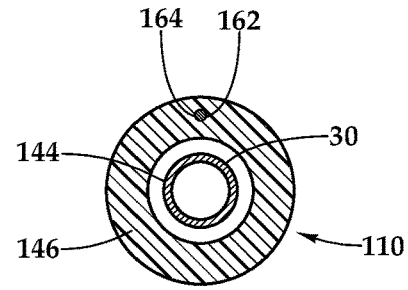
FIG. 9 is an end full sectional view of that which is shown in FIG. 7.

FIG. 9 depicts the embodiment of FIG. 7 in a full sectional end view, according to one embodiment where the wire 162 and insulation jacket 164 are embedded within the outer insulation 146, rather than merely having the outer insulation 46 wrapped outside of the wire 162.

Figure 8:
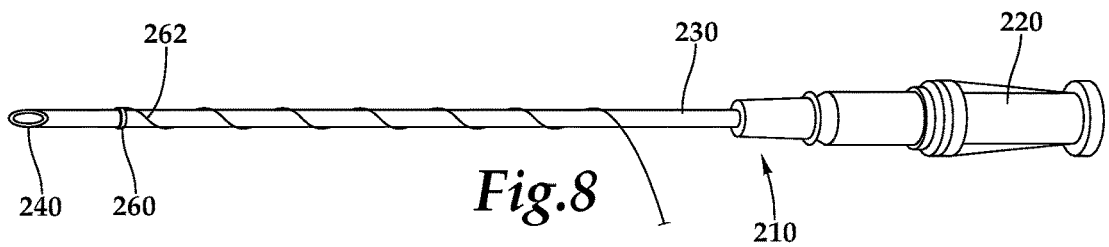
FIG. 8 is a perspective view of a modified version of that which is shown in FIG. 7.

FIG. 8 depicts a unipolar electrode needle 210. This unipolar electrode needle 210 includes a hub 220 with a shaft 230 of the needle 210 extending away from the hub 220 to a tip 240. A proximal electrode 260 is coupled to the shaft 230 a known distance away from the tip 240. A wire 262 extends from the proximal electrode 260 and is fed into the EP mapping system 2 (FIG. 1). Unipolar electrodes such as the proximal electrode 260 function by being coupled with some other electrode within the EP mapping system 2 or associated with some portion of the needle 210, or some other reference, so that meaningful information can be gathered with regard to the position (and preferably also orientation) of the needle 210.

In the embodiment depicted in FIG. 8, the wire 262 is merely wrapped around the exterior of the shaft 230, but could be covered with an outer insulation player, embedded within the shaft 230 or otherwise conveniently routed, or wiring could be dispensed with should be unipolar electrode 260 be fitted with a micro-mechanical power source of some form and a transmitter and other electronics to allow it to function as an electrode without an associated wire 262.

Figure 10:
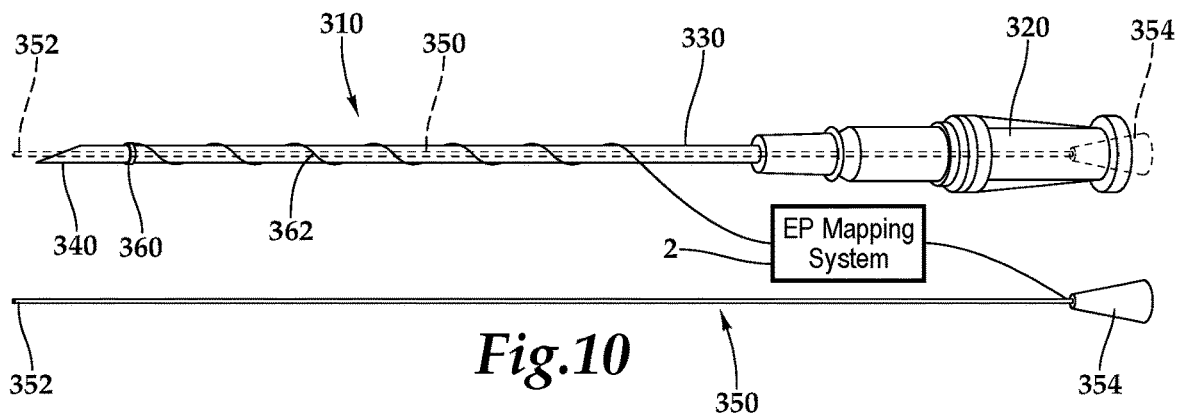
FIG. 10 is a perspective view of an embodiment of that which is shown in FIG. 3 where a single electrode is placed upon the needle and a stylet electrode is associated with the needle, the stylet electrode shown exterior to the needle and shown in broken lines placed within the needle.

With particular reference to FIG. 10, details of a needle/stylet 310 combination are described. In this embodiment a hub 320 supports a shaft 330 extending out to a tip 340, similar to the needle 10 depicted in FIG. 3. However, only one electrode in the form of a proximal electrode 360 is provided on this shaft 330 spaced a known distance away from the tip 340. Wire 362 preferably extends from this proximal electrode 360 and is fed to the EP mapping system 2. A stylet 350 is also coupled to the EP mapping system 2 and has a distal end 352 opposite a base 354. The stylet 350 is preferably sufficiently long that the distal end 352 of the stylet 350 can pass entirely through a hollow center of the shaft 330 and extend out of the tip 340. The stylet 350 is preferably formed of electrically conductive material so that the distal end 352 can act as an electrode in this embodiment. As an alternative (or in addition), one or more magnetic field sensors can be placed on the stylet to convey its position (and preferably also orientation within the EP mapping system 2).

Preferably the shaft 330 is formed of electrically nonconductive material. As an alternative, the stylet 350 can have an outer insulative jacket formed of electrically nonconductive material or an interior of the shaft 330 can be coated with or otherwise lined with electrically non-conductive material. Between the distal end 352 of the stylet 350 and the proximal electrode 360, the combined needle/stylet 310 can function similar to a dual electrode needle such as that disclosed in FIGS. 1-6. The stylet 350 is movable relative to the shaft 330. The distal end 352 of the stylet 350 can be provided as a blunt tip, or with a sharpened tip, and with the tip 340 of the shaft 330 configured either to be sharp or somewhat blunted, so the various different functionalities can be provided between the shaft 330 and stylet 350 as is known in the stylet and needle arts as they pertain to cardiac surgery and related medical procedures and devices.

Figure 11:
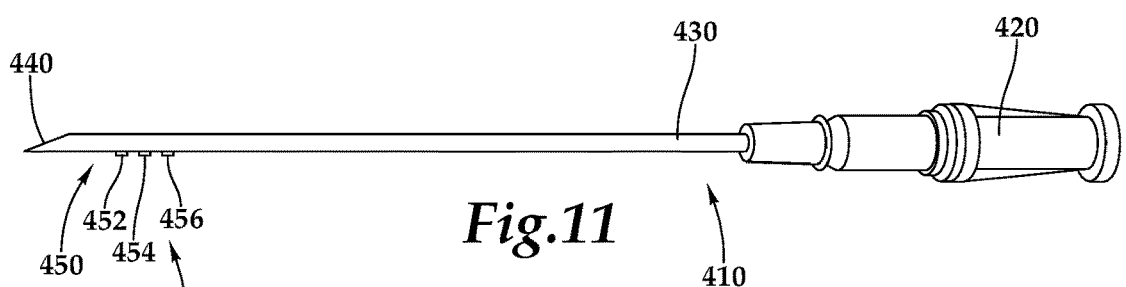
FIG. 11 is a perspective view of an embodiment of that which is shown in FIG. 3 which utilizes magnetic field sensors rather than electrodes, such as for use within the EP mapping system of FIG. 2.

With particular reference to FIG. 11, a needle 410 is disclosed which includes sensors which are preferably in the form of a magnetic field sensor set 450. The needle 410 includes a hub 420 upon which a shaft 430 is supported and extending out to a tip 440. The magnetic field sensor set 450 preferably includes three separate magnetic field sensors 452, 454, 456, such as sensors oriented in three mutually perpendicular orientations (e.g. X, Y and Z axes), so that the magnetic field from the sources 9 (FIG. 2) can be most accurately characterized at the location adjacent to this magnetic field sensor set 450. For simplicity, the sensors 452, 454, 456 are identified as boxes along a line, but could be oriented non-linearly and would most typically be solenoids or other coils with a generally cylindrical form.

Position (and preferably also orientation) can be ascertained based on a sensed intensity of the magnetic field relative to sources 9 (FIG. 2) of the magnetic field, and the position of bodily structures, and particularly cardiac structures which can be identified by electrodes, other magnetic sensors, other imaging systems, or combinations thereof. Thus, a position of the needle 410 fitted with the magnetic field sensor set 450 can be accurately determined and then displayed on the display 8 of the EP mapping system 2 (FIG. 2).

Figure 12:
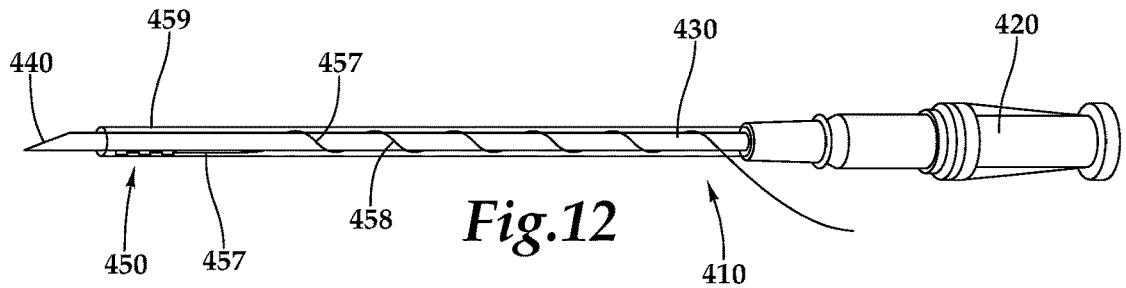
FIG. 12 is a perspective view of a modified version of that which is shown in FIG. 11.

Other details of the needle 410 are preferably similar to those disclosed above with respect to FIGS. 1 and 3-5. In this embodiment, for simplicity, no wires are shown, but typically, and as depicted in FIG. 12, the sensor set 450 would have at least one wire 457 extending therefrom (and optionally three wires in some embodiments) one to each individual sensor 452, 454, 456, and preferably with an insulation jacket 458 outboard of the wire 457 and within a jacket 459 surrounding the wires 457 and holding them adjacent to the shaft 430 of the needle 410, as depicted in FIG. 12, as one example.

Figure 13:
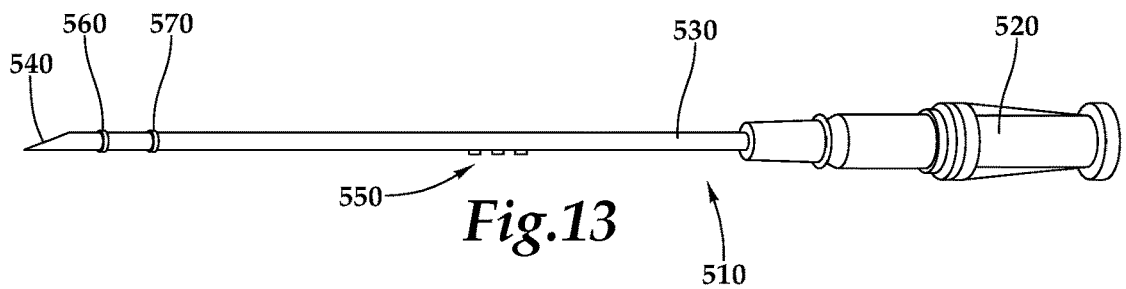
FIG. 13 is a perspective view of an alternative embodiment of that which is shown in FIG. 11 where the magnetic field sensors are located more proximal to a hub of the needle, and with optional electrodes are added to the needle so that a hybrid collection of magnetic field sensors and electrodes are provided together on a common needle, according to this embodiment.

With particular reference to FIG. 13, a hybrid needle 510 is disclosed that utilizes both magnetic field sensors 550 and at least one electrode 560, 570. In the embodiment depicted, a needle 510 includes a hub 520 with a shaft 530 extending therefrom to a tip 540. The shaft 530, includes a sensor, typically at any location thereon, but in the example depicted slightly closer to the hub 20 than to the tip 540, in the form of a magnetic field sensor set 550. Additionally, at least one electrode, and preferably both a distal electrode 560 and a proximal electrode 570 are also located upon the shaft 530. While wires are not depicted, they would typically extend from these sensors in the form of the magnetic field sensor set 550, as well as from the electrodes 560, 570. Information from the sensors is passed on to the EP mapping system 2 for most accurate visualization of the needle 510.

Figure 14:
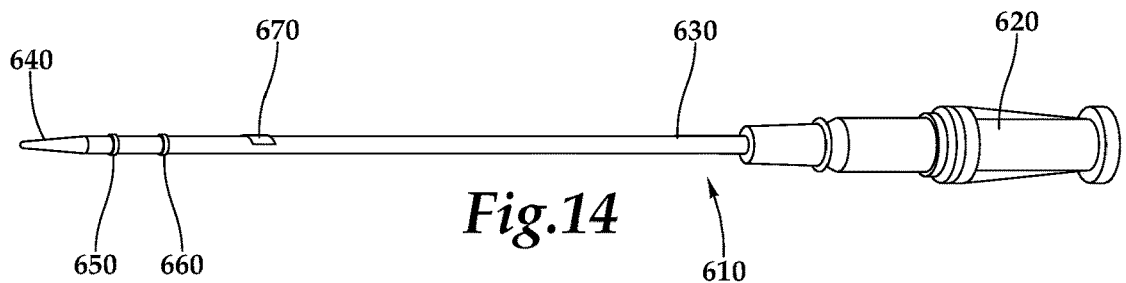
FIG. 14 is a perspective view of a dilator with electrodes thereon for visualization within an EP mapping system such as that disclosed in FIG. 1.

With particular reference to FIG. 14, an embodiment of this invention is depicted where a dilator 610 is fitted with electrodes 650, 660 as one form of sensor to allow for visualization of the dilator 610 within an EP mapping system 2. The dilator 610 includes a hub 620 with a shaft 630 extending therefrom to a tip 640. In this disclosed embodiment, two electrodes 650, 660 are coupled to the shaft 630 at known distances away from the tip 640. A force sensor 670 can also be provided. As one option, one of these electrodes 650 could be located at the tip 640. Typically wires extend from these electrodes 650, 660 and force sensor 670 and appropriate insulation is provided to keep these wires extending from the electrode 650, 660 from shorting out each other as they are routed back to the EP mapping system 2. With such a dilator 610, dilator placement can be most effectively controlled utilizing the EP mapping system 2, and particularly the display 8 thereof, to guide a surgeon S or other medical professional in the placing of the dilator 610 where desired.

With particular reference to FIGS. 15 and 16, two variations on a sheath, including a straight sheath 710 and a curved sheath 810 are disclosed. Shafts 730, 830 are either straight or curved, extending out to tips 740, 840. Hubs 720, 820 are provided opposite these tips 740, 840. With these sheaths 710, 810 valves 725, 825 are preferably provided at the hubs 720, 820 for placement of a dilator or other structure therethrough during a placement (also known as "introduction") procedure. Such devices are also referred to as introducers. A separate fluid control line typically interfaces with the hubs 720, 820, in the form of fluid manifolds 727, 827 to allow for fluid flow after placement of the sheaths 710, 810 where desired. Sensors, depicted in these embodiments as magnetic field sensor sets 750, 850 are provided upon the shafts 730, 830, and preferably adjacent to the tips 740, 840, which allow for a location of these sheaths, and particularly tips thereof, to be visualized through a display 8 of an EP mapping system 2 and for placement where desired. In addition to sheaths 710, 810 other medical devices can similarly be fitted with sensors to facilitate their viewing on a display 8 of an EP mapping system 2. Such other devices include catheters, scalpels, ablation tools, biopsy needles, shunts, drain tubes, etc.

This disclosure is provided to reveal a preferred embodiment of the invention and a best mode for practicing the invention. Having thus described the invention in this way, it should be apparent that various different modifications can be made to the preferred embodiment without departing from the scope and spirit of this disclosure. When structures are identified as a means to perform a function, the identification is intended to include all structures which can perform the function specified.

What is claimed is:

1. A patient cardiac visualization system, comprising in combination:
   a cardiac electrophysiology mapping subsystem located proximate to a patient's heart for visualizing a cardiac region of the patient;
   a needle including at least one sensor thereon;
   said sensor on said needle interfacing with said cardiac electrophysiology mapping subsystem to identify a location of said needle within the cardiac space of the patient; and
   wherein a tip of said needle is located a known distance from said at least one sensor on said needle, said needle including a shaft extending along a central axis, with said at least one sensor at a sensor position on said shaft and said tip spaced away from said sensor position by an offset amount, and wherein said cardiac electrophysiology mapping subsystem displays an accurate location of said tip of said needle, said location spaced away from said sensor position by said offset amount along said central axis of said shaft, within a visualization of the cardiac region of the patient provided by said electrophysiology mapping subsystem.

2. The system of claim 1 wherein said at least one sensor is a magnetic sensor and wherein said cardiac electrophysiology mapping subsystem includes an artificial magnetic field proximate to the patient's heart.

3. The system of claim 1 wherein said at least one sensor includes an electrode, and wherein said cardiac electrophysiology mapping subsystem includes a plurality of electrodes proximate to the patient's heart to induce an electric field proximate to the patient's heart.

4. The system of claim 3 wherein said needle includes at least two electrodes thereon and wherein said at least two electrodes interface with said cardiac electrophysiology mapping subsystem to display both a position and an orientation of said needle within the cardiac space of the patient.

5. The system of claim 1 wherein said at least one sensor includes at least two electrodes, with said tip of said needle being one of said at least two electrodes.

6. The system of claim 1 wherein said needle has a rigid form between said sensor and a tip of said needle.

7. The system of claim 6 wherein said tip of said needle is pointed, with a smaller diameter than other portions of said needle spaced from said tip.

8. The system of claim 1 wherein said needle is a pericardiocentesis needle.

9. The system of claim 1 wherein said electrophysiology mapping subsystem displays an animation of a virtual needle on a display thereof.

10. A system for visualizing a location of a needle within a subcutaneous cardiac space of a patient, the system comprising in combination:
   a display configured to display a three-dimensional rendering of the cardiac space of the patient with a plurality of subcutaneous patient structures in the cardiac space accurately displayed on the display relative to other structures within the cardiac space;
   said display coupled to output of a cardiac electrophysiology mapping subsystem;
   a needle having at least one sensor thereon, said needle coupled to said cardiac electrophysiology mapping subsystem, said sensor causing said needle to have its position within the cardiac space identified on said display; and
   wherein said at least one sensor is located a known distance from a tip of said needle, said needle including a shaft extending along a central axis, with said at least one sensor at a sensor position on said shaft and said tip spaced away from said sensor position by an offset amount, and wherein said cardiac electrophysiology mapping subsystem displays an accurate location of said tip of said needle, said location spaced away from said sensor position by said offset amount along said central axis of said shaft, within a visualization of the cardiac region of the patient provided by said electrophysiology mapping subsystem.

11. The system of claim 10 wherein said at least one sensor is a magnetic sensor and wherein said cardiac electrophysiology mapping subsystem includes an artificial magnetic field proximate to the patient's heart.

12. The system of claim 10 wherein said at least one sensor includes an electrode, and wherein said cardiac electrophysiology mapping subsystem includes a plurality of electrodes proximate to the patient's heart to induce an electric field proximate to the patient's heart.

13. The system of claim 12 wherein said needle includes at least two electrodes thereon and wherein said display shows both a position and orientation of said needle accurately relative to other subcutaneous patient structures in the cardiac space.

14. The system of claim 10 wherein said at least one sensor includes at least two electrodes, with said tip of said needle being one of said at least two electrodes.

15. The system of claim 10 wherein said needle has a rigid form between said sensor and a tip of said needle.

16. The system of claim 15 wherein said tip of said needle is pointed, with a smaller diameter than other portions of said needle spaced from said tip.

17. The system of claim 10 wherein said needle is a pericardiocentesis needle.

18. The system of claim 10 wherein said electrophysiology mapping subsystem displays an animation of a virtual needle on a display thereof.

* * * * *